United States Patent
Danger

(10) Patent No.: US 9,017,076 B2
(45) Date of Patent: Apr. 28, 2015

(54) METHOD OF CONTROLLING A DRIVE DEVICE FOR PREPARING A ROOT CANAL, AND ROTATING HANDPIECE FOR ROOT CANAL PREPARATION

(75) Inventor: Karl-Heinz Danger, Detmold (DE)

(73) Assignee: Gebr. Brasseler GmbH & Co. KG (DE)

( * ) Notice: Subject to any disclaimer, the term of this patent is extended or adjusted under 35 U.S.C. 154(b) by 0 days.

(21) Appl. No.: 13/535,933

(22) Filed: Jun. 28, 2012

(65) Prior Publication Data

US 2013/0004913 A1    Jan. 3, 2013

(30) Foreign Application Priority Data

Jun. 29, 2011 (DE) .......................... 10 2011 105 958

(51) Int. Cl.
*A61C 5/02* (2006.01)
*A61C 1/00* (2006.01)

(52) U.S. Cl.
CPC .. *A61C 1/003* (2013.01); *A61C 5/02* (2013.01)

(58) Field of Classification Search
CPC .............. A61C 1/085; A61C 3/02; A61C 3/04
USPC ............... 433/224, 102, 165, 81, 215
See application file for complete search history.

(56) References Cited

U.S. PATENT DOCUMENTS

| | | | |
|---|---|---|---|
| 5,104,316 A | 4/1992 | McSpadden | |
| 5,944,523 A | 8/1999 | Badoz | |
| 6,293,795 B1 | 9/2001 | Johnson | |
| 2003/0013067 A1* | 1/2003 | Bleiweiss et al. | 433/102 |
| 2010/0040994 A1* | 2/2010 | Johnson | 433/132 |
| 2012/0122055 A1* | 5/2012 | Ramos et al. | 433/102 |

FOREIGN PATENT DOCUMENTS

| | | |
|---|---|---|
| DE | 1 112 810 | 8/1961 |
| DE | 697 31 996 | 12/2005 |
| DE | 60032144 | 4/2007 |
| EP | 0118992 | 9/1984 |
| EP | 0812578 | 12/1997 |
| EP | 1 196 109 | 4/2002 |
| WO | 01/03601 | 1/2001 |
| WO | 2010/109464 | 9/2010 |

OTHER PUBLICATIONS

European Search Report dated Nov. 27, 2012 from counterpart application.

* cited by examiner

*Primary Examiner* — Yogesh Patel
(74) *Attorney, Agent, or Firm* — Timothy J. Klima; Shuttleworth & Ingersoll, PLC

(57) ABSTRACT

A method, and handpiece for performing the method, for controlling a drive device for moving a root canal instrument having a drive shaft and at least one cutting edge for preparing a root canal, and at least one drive motor being operated by a control unit. The root canal instrument is moved in at least one reciprocal movement in a first direction of rotation over a predetermined first angle of rotation and subsequently in a second direction of rotation opposite to the first direction of rotation over a predetermined second angle of rotation. After the at least one reciprocal movement, the root canal instrument is rotated over at least one third angle of rotation.

15 Claims, 2 Drawing Sheets

METHOD OF CONTROLLING A DRIVE DEVICE FOR PREPARING A ROOT CANAL, AND ROTATING HANDPIECE FOR ROOT CANAL PREPARATION

This application claims priority to German Patent Application DE102011105958.3 filed Jun. 29, 2011, the entirety of which is incorporated by reference herein.

It is known from the prior art that for the preparation of root canals of teeth, the root canal instrument is driven in an appropriate rotational movement. There is the need to choose the rotational movement and/or a longitudinal movement longitudinally to the axis of rotation of the root canal instrument in such a manner that high loads on the root canal instrument which are not desired and might lead to breakage of the root canal instrument are avoided. Furthermore, the movement of the root canal instrument in the root canal has to be chosen such that the cutting edges of the root canal instrument are in cutting engagement for the preparation thereof and that the material cut off by the cutting edges can be removed from the root canal.

In mechanical drives of root canal instruments the prior art shows reciprocal movements that are fixedly predetermined by the mechanical configuration of a drive device. Reference is here made to DE 697 31 996 T2.

A further possible movement of the root canal instrument is shown in EP 1 196 109 B1. In a pilgrim step method one movement is continuously carried out over one direction of rotation and subsequently one movement is carried out in the opposite direction of rotation over a smaller angle of rotation. These motion sequences are repeated continuously and sequentially. DE 1 112 810 A also shows a pilgrim step-like motion of a root canal instrument.

The methods known from the prior art have the drawback that overloading and thus failure of the root canal instrument cannot be reliably prevented and that the movement performed for the successful preparation of the root canal and/or for the discharge of chips or removed material is not perfect.

It is an object of the present invention to provide a method of controlling a drive device for moving a root canal instrument and a rotating handpiece for preparing a root canal which, while being of a simple structure and easy to produce at low costs, avoids the drawbacks of the prior art and leads to optimum work results.

As for the method according to the invention, it is thus intended that for the control of a drive device for the movement of a root canal instrument provided with at least one cutting edge for the preparation of a root canal, a drive device is used which comprises at least one drive motor, which is preferably configured as a stepping motor or a servo motor, as well as a control unit.

The drive device which is used according to the invention in the method can be connected via a cable to a separate power supply and to the control unit. It is, however, also possible to use a battery-operated hand-held device in the case of which the control unit and also suitable input and control devices for the manual operation are provided.

According to the invention, it is thus further intended with respect to the method that the root canal instrument is moved in at least one reciprocal movement in a first direction of rotation over a predetermined first angle of rotation and subsequently in a second direction of rotation opposite to the first direction of rotation over a predetermined second angle of rotation. In an advantageous configuration of the invention, it is intended that the first and the second angle of rotation have the same values. This is, however, not absolutely necessary according to the invention.

An advantage of the method according to the invention is that the chips and the cut-off material can be reliably removed from the root canal. By contrast the solutions known from the prior art pose the risk that chips are transported in the direction of the apex of the root, resulting in clogging at that place. Such a clogging must subsequently be removed again in very complicated work steps (rinsing) according to the prior art.

In the method according to the invention, the root canal instrument is reciprocally moved to and fro about its axis of rotation. As has been mentioned, this reciprocal to-and-fro movement is preferably implemented in such a manner that the two angles of rotation are identical.

According to the invention, it is possible to provide only such a reciprocal movement before a rotation around a third angle of rotation is carried out, as shall be described hereinafter. It is, however, also possible to carry out several reciprocal movements of that type. When performing a plurality of such reciprocal movements, it is also possible to choose different values for the individual angles of rotation. It is particularly advantageous when the selection of the angles of rotation is controlled by a random generator. It is thus possible to provide very different angles of rotation in random sequence. After at least one reciprocal movement has now been carried out in the method according to the invention, the root canal instrument is rotated over a third angle of rotation. An additional rotational movement is thereby applied through the third angle of rotation. This may e.g. be 360°, but it is also possible to choose the third angle of rotation such that it is smaller or greater than 360°. It is also possible according to the invention to configure the third angle of rotation such that the root canal instrument carries out several full rotations (360° several times). The third angle of rotation can also be chosen according to the invention by way of the random generator.

The method according to the invention thereby makes it possible that the at least one cutting edge of the root canal instrument shows a cutting or removing action during the reciprocal movement and that subsequently a greater cutting or removing movement is carried out about a greater angle, e.g. 360° or a multiple thereof. Due to this sequence of cutting movements the root canal is reliably prepared on the one hand. It is ensured on the other hand that the cut-off materials or chips are reliably discharged out of the root canal so that the canal cannot get clogged and that the root canal instrument does not squeeze. Thanks to the prevention of a squeezing action, overloading of the root canal instrument can be avoided, so that the risk of breakage is considerably reduced.

According to the invention a combined movement is provided, namely a reciprocal one with a subsequent 360° movement. Hence, the drive device carries out the root canal preparation reciprocally at the beginning and in a program-controlled manner. This achieves a higher dosed removal rate. In the last interval of the root canal preparation a switching operation to a 360° rotation is then carried out according to the program. Alternatively, it is also possible according to the invention to make use of a 360° movement not only in the last interval of the root canal preparation, but already after a few or after only one reciprocal movement in an automatic and program-controlled way, so that a combination of both movements can be carried out, depending on the situation or the idea of the treating dentist. As has been said, irregular reciprocal movements can also be implemented and these may also be coupled with a 360° rotation. This results in random movements which are controlled by the random generator. This improves the removal behavior of the root canal instrument. It is here particularly advantageous when the rotary reversal in reciprocal movements does not always take place within the same angular range, so that one avoids situations where steps or recesses are produced.

In an advantageous development of the invention, it is intended that the selection of the angles of rotation, particularly of the first and the second angle of rotation, is made dependent on the position of the instrument relative to the apex. This can be done through a superposed length measurement or position measurement of the instrument. This ensures an optimal root canal preparation. In a development of this configuration variant it may be provided that near the apex one changes to a full rotation of the root canal instrument, with a reduced torque being here applied. This configuration variant can also be adopted alone, without the aforementioned positional dependence on the apex.

According to the invention, the movement mechanisms can permit, apart from a circular round preparation, also e.g. an oval root canal preparation because the root canal instruments also permit a lateral removal in the case of a uniform reciprocal movement or a reciprocal movement which is controlled by a random generator.

Movements in a radial direction are additionally advantageous according to the invention. This can improve the removal rates in specific areas of the root canal. Furthermore, the chips which automatically collect in the chip spaces of the root canal instrument during abrasion can be removed. It should particularly be taken into account here that root canal instruments have very small diameters and that the chip spaces are thus also very limited. According to the invention, this makes it possible to create very different motion combinations, e.g. combinations of reciprocal and axial to-and-fro movements and/or reciprocal and a 360° rotation and/or a radial to-and-fro movement or 360° rotation, respectively, and/or radial to-and-fro movements in uniform movements or controlled by a random generator.

Root canal instruments with one cutting edge, with two cutting edges or with several cutting edges may be used by means of the method according to the invention.

Preferably, the method according to the invention is used in a root canal instrument set according to the crown-down method in which a first instrument has a larger diameter than the respectively successive instrument and in which the root canal is prepared, starting from the crown, in an expanding way. It is, however, also possible according to the invention to use the method according to the invention in only one root canal instrument and e.g. to drive the remaining root canal instruments of the set in a conventional way. Furthermore, it is also possible according to the invention to use the method in a root canal instrument set in which first of all a thinner first root canal instrument is used whereas the respectively successive root canal instrument has a larger diameter.

According to the invention, the third angle of rotation may have the same or an opposite direction of rotation as compared with the second direction of rotation. This is especially of advantage in the case of root canal instruments in which the cutting edges are operative in both directions of rotation in a bearing or cutting manner.

As has already been mentioned in a few words, the first angle of rotation and the second angle of rotation for different reciprocal movements are given different or identical values. The value of the respective angle of rotation can be chosen by the random generator in an appropriate way such that a "random" rotational movement of the root canal instrument is obtained in the root canal. This leads to considerably improved work results.

In a preferred development of the invention, it is also possible to choose the first angle of rotation, the second angle of rotation, and the third angle of rotation, each in response to the load arising in the root canal instrument, particularly in response to the torque applied to the root canal instrument. This selection can also preferably be made via the random generator. It is thereby ensured that the root canal instrument is always below its critical load limit.

In a further advantageous development of the invention, it may be provided that the first angle of rotation and/or the second angle of rotation have a value which is matched to the number of the cutting edges of the root canal instrument. For instance, the angle of rotation may be $$\frac{360°}{n}$$

each time, where n is the number of the cutting edges of the root canal instrument. Hence, a uniform preparation of the root canal is carried out by all cutting edges of the root canal instrument, wherein the cutting edges are each moved to and fro over a predetermined angular range. It goes without saying that also a slightly greater angular range may be provided so as to provide for an overlapping of the individual work areas of the cutting edges of the root canal instrument.

In addition to the above-explained rotational movement of the root canal instrument, it is also particularly advantageous according to the invention when the instrument is moved in a longitudinal movement along its rotational axis. A reciprocal to-and-fro movement may here be carried out, the magnitude of which can also be determined by the random generator. For instance, lifting movements with an amplitude of about 2 mm are advantageous. The longitudinal lifting movement may be carried out as a separate movement after the reciprocal movement or the rotation about the third angle of rotation. It is, however, also possible to provide for the reciprocating longitudinal movement during the movement about the first or second angle of rotation and/or during the movement about the third angle of rotation.

Hence, with the method according to the invention a movement of the root canal instrument is applied in the root canal by the random generator by way of an appropriate selection of the rotational angles and rotational movements, which movement results in a very efficient mode of operation of the root canal instrument.

The invention will now be described with reference to embodiments in combination with the drawings, in which.

Figure 1:
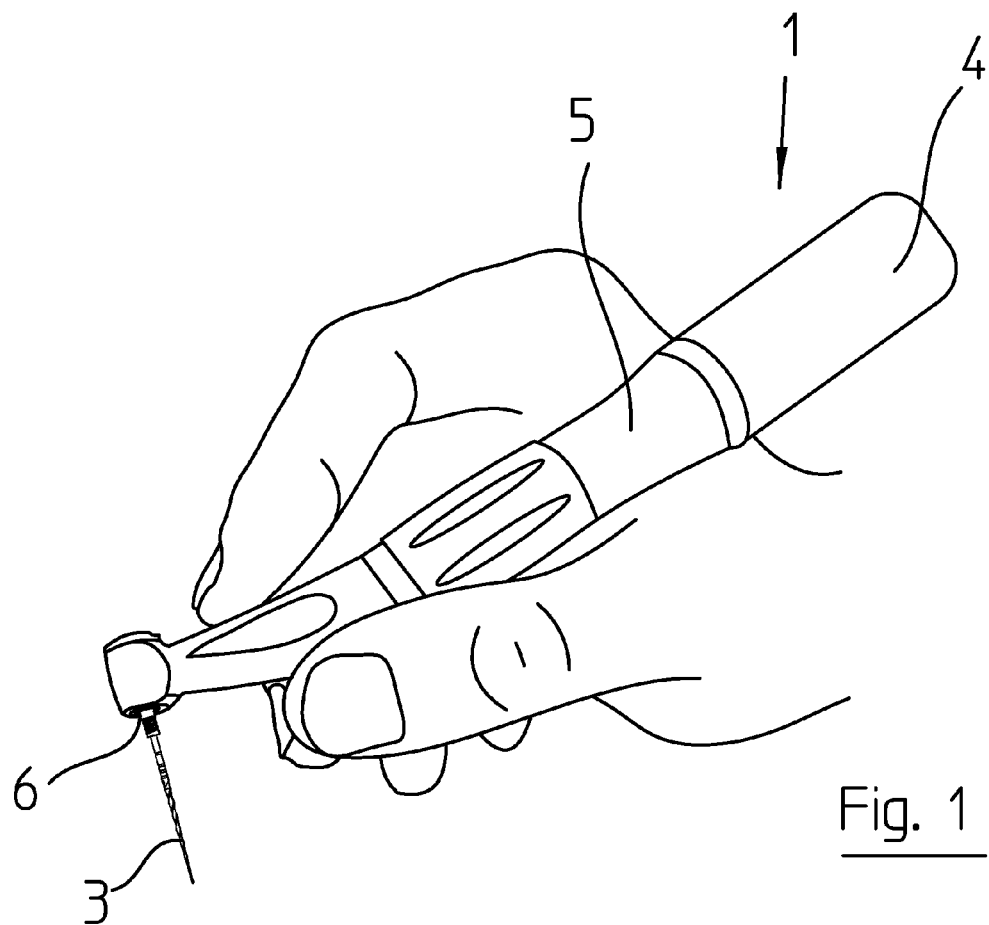
FIG. 1 is a simplified perspective view of the drive device according to the invention with a root canal instrument.

FIG. 1 is s simplified view showing a drive device 1 which in the illustrated embodiment is configured without a cable and comprises a drive motor 4 and a control unit 5. An operation can be carried out by an operator by way of pushbuttons or switches. A power supply is provided through a battery. As an alternative, the drive device may also be provided with a cable and a separate control unit and an external power supply.

The drive device 1 comprises a driven shaft 6 with which a root canal instrument 3 is coupled for rotation therewith in the standard way.

Figure 2:
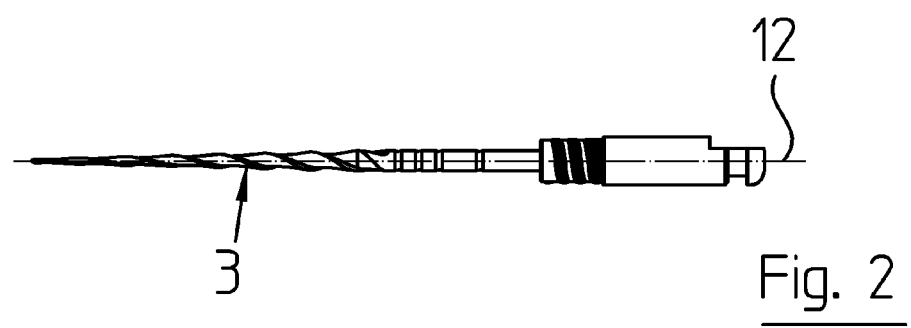
FIG. 2 is an enlarged side view of a root canal instrument which can be used according to the invention.

FIG. 2 is a schematic side view showing a root canal instrument 3 which can be used according to the invention and may be configured in the way known from the prior art.

Figure 3:
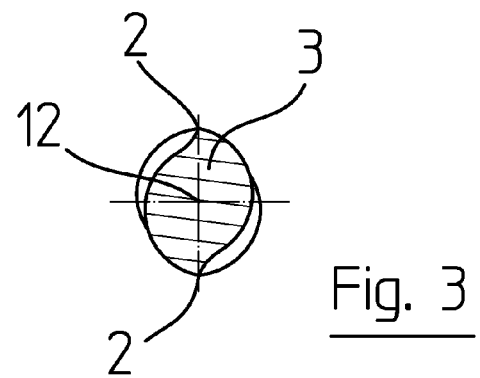
FIG. 3 is a sectional view through the work area of the root canal instrument shown in FIG. 2.

FIG. 3 is a sectional view through the work area; the two cutting edges 2 are here shown.

Figure 4:
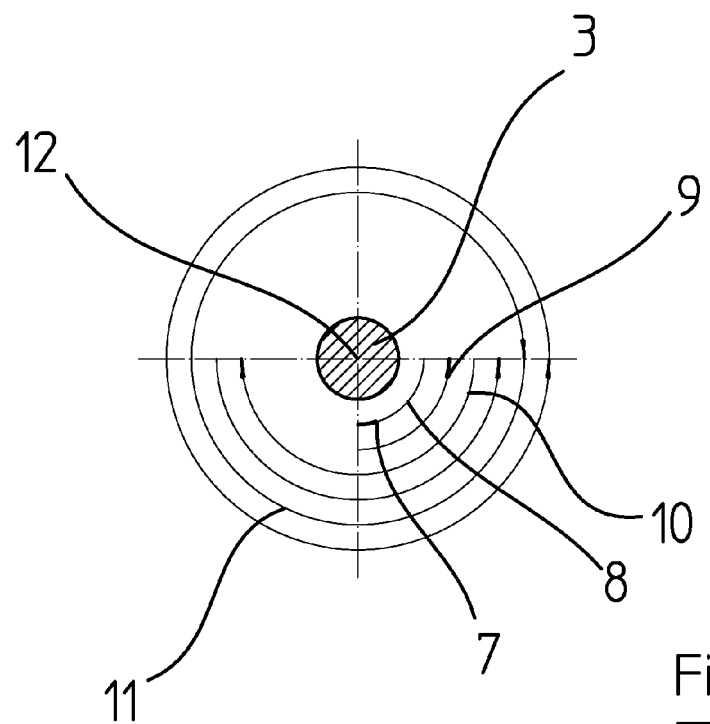
FIG. 4 is a simplified illustration of the rotational movements according to the invention.

FIG. 4 is a schematic illustration with a view on the rotational axis 12 in a similar illustration as in FIG. 3. It is shown here that a rotation of the root canal instrument 3 about its axis of rotation 12 is first carried out in a first direction of rotation 7 about a first angle of rotation 8. Subsequently, a reciprocal movement is carried out in a second direction of rotation 9 about a second angle of rotation 10. In the illustrated embodiment, the two angles of rotation 8 and 10 are each time the same and amount to 90°. It is, however, also possible to provide other angles of rotation, as is e.g. shown in FIG. 5. The first and the second angle of rotation are here 120° each.

Figure 5:
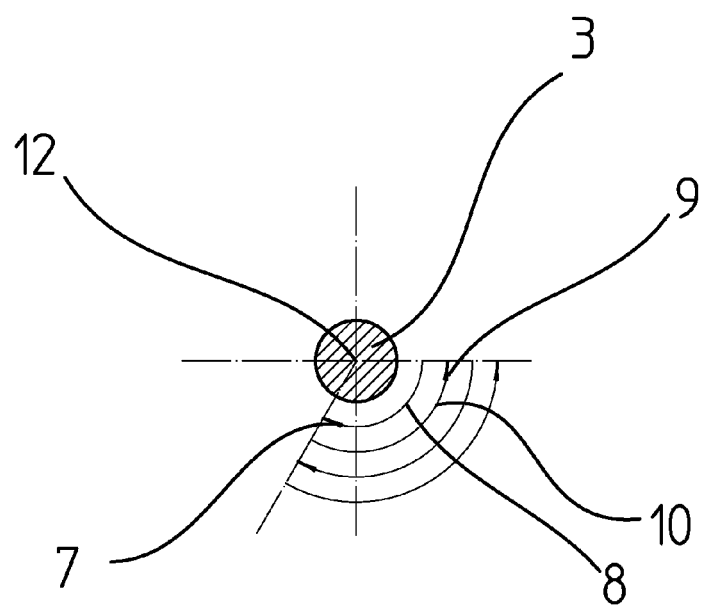
FIG. 5 is a view, by analogy with FIG. 4, of a further embodiment of the rotational movement according to the invention.

As shown in FIG. 5, it is possible to provide a plurality of such reciprocal movements about identical angles of rotation. FIG. 5 shows two reciprocal motional sequences of that type.

In the embodiment shown in FIG. 4, a further reciprocal movement about a further angle of rotation of 180° is carried out after the reciprocal movement about the first angle of rotation 8 and the second angle of rotation 10. After completion of the reciprocal rotational movements a rotation of the root canal instrument is carried out about a third angle of rotation 11 which is 360°. Subsequently, a further rotation by 360° may be carried out in the reverse direction of rotation.

Hence, according to the invention, the random generator creates the possibility of carrying out any desired sequences of reciprocal movements and rotations about the third angle of rotation. Both the angular amounts of the first and the second angle of rotation and of the third angle of rotation are here chosen by the random generator. Hence, a purely random movement of the root canal instrument can be carried out, namely random reciprocal movements (to-and-fro movements) about identical or different angles of rotation and third rotational movements about third angles of rotation, e.g. 360°, 270°, or the like. The sequence of the individual rotational movements can here also be predetermined by the random generator.

LIST OF REFERENCE NUMERALS

1 Drive device
2 Cutting edge
3 Root canal instrument
4 Drive motor
5 Control unit
6 Drive shaft
7 First direction of rotation
8 First angle of rotation
9 Second direction of rotation
10 Second angle of rotation
11 Third angle of rotation
12 Rotational axis

The invention claimed is:

1. A method of controlling a drive device for moving a root canal instrument provided with at least one cutting edge for preparing a root canal and a drive shaft connected to a drive motor controlled by a programmed controlled unit, wherein the programmed control unit controls the drive motor to: move the root canal instrument in at least one reciprocal movement in a first direction of rotation over a predetermined first angle of rotation and subsequently in a second direction of rotation opposite to the first direction of rotation over a predetermined second angle of rotation;

after the at least one reciprocal movement, rotate the root canal instrument over at least one third angle of rotation; and near an apex of a root of a tooth, begin full rotation of the root canal instrument with a reduced torque as compared to a torque during a preceding angle of rotation.

2. The method according to claim 1, wherein the third angle of rotation has at least one of an identical or an opposite direction of rotation as the second direction of rotation or an angle of rotation of at least 360°.

3. The method according to claim 2, wherein the first and the second angles of rotation have different magnitudes.

4. The method according to claim 3, wherein at least one chosen from the first and the second angles of rotation and the third angle of rotation are randomly selected.

5. The method according to claim 4, wherein the at least one chosen from the first and the second angle of rotation and the third angle of rotation are randomly selected by at least one of a random generator or in response to a torque acting on the root canal instrument.

6. The method according to claim 2, wherein the first and the second angles of rotation have identical magnitudes.

7. The method according to claim 1, wherein the first and the second angles of rotation have a value which is $$\frac{360°}{n},$$

where n is the number of the cutting edges of the root canal instrument.

8. The method according to claim 1, wherein any of the angles of rotation can be varied in dependence upon a position of the root canal instrument relative to the apex of the root.

9. The method according to claim 8, wherein the any of the angles of rotation can be varied in dependence upon the position of the root canal instrument relative to the apex of the root by superposed length measurement.

10. The method according to claim 1, wherein the at least one of the angles of rotation is changed near the apex of the root to full rotation with the reduced torque by superposed length measurement.

11. The method according to claim 1, wherein the root canal instrument is moved to and fro in a longitudinal movement along its axis of rotation, and the longitudinal movement is carried out during or after the reciprocal movement or during or after the movement about the third angle of rotation.

12. The method according to claim 1, wherein the first and the second angles of rotation have different magnitudes.

13. The method according to claim 1, wherein the first and the second angles of rotation have identical magnitudes.

14. The method according to claim 1, wherein at least one chosen from the first and the second angles of rotation and the third angle of rotation are randomly selected.

15. The method according to claim 14, wherein the at least one chosen from the first and the second angle of rotation and the third angle of rotation are randomly selected by at least one of a random generator or in response to a torque acting on the root canal instrument.

* * * * *